United States Patent [19]
Pifferi et al.

[11] Patent Number: 5,120,730
[45] Date of Patent: Jun. 9, 1992

[54] BENZOTHIAZEPINE ESTERS, THEIR PREPARATION AND FORMULATIONS FOR THERAPEUTIC USE

[75] Inventors: Giorgio Pifferi; Rita Nizzola; Salvatore Malandrino, all of Milan, Italy

[73] Assignee: IdB Holding SpA, Milan, Italy

[21] Appl. No.: 713,788

[22] Filed: Jun. 12, 1991

[30] Foreign Application Priority Data

Jun. 21, 1990 [GB] United Kingdom ............... 9013878

[51] Int. Cl.$^5$ ................. A61K 31/55; C07D 281/02
[52] U.S. Cl. ................................. 514/211; 540/491
[58] Field of Search .................... 540/491; 514/211

[56] References Cited

U.S. PATENT DOCUMENTS 3,562,257  2/1971  Kugita et al. ...................... 540/491

OTHER PUBLICATIONS

*Merck Index*, 11th edition, 1989, Merce & Co., Rahway, N.J., p. 505, item 3188.
Joslyn et al., *J. Med. Chem.*, vol. 31, pp. 1489–1492 (1988).

*Primary Examiner*—Robert T. Bond
*Attorney, Agent, or Firm*—Kirschstein, Ottinger, Israel & Schiffmiller

[57] ABSTRACT

A class of benzothiazepine esters having structures related to that of diltiazem are provided which possess vasodilating activity while being virtually free of cardiodepressive effects. The esters are useful in the treatment of arterial hypertension and disturbances of the cerebral circulation.

The compounds have the general formula I

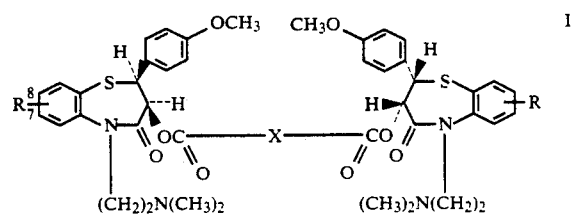

wherein
R represents hydrogen or an electronegative group (preferably a halogen atom, or a nitro, trifluoromethyl or methoxy group); and
X is a hydrocarbyl group containing from 1 to 15 carbon atoms.

8 Claims, No Drawings

BENZOTHIAZEPINE ESTERS, THEIR PREPARATION AND FORMULATIONS FOR THERAPEUTIC USE

The present invention relates to novel benzothiazepine esters, processes for their preparation and formulations for therapeutic use.

(+)-Cis-5-[2-(dimethylamino)ethyl]-3-acetoxy-2,3-dihydro-2-(4-methoxyphenyl)-1,5-benzothiazepin-4(5H)-one (known as diltiazem) is the parent compound of an important class of calcium antagonists which are capable of reducing the intracellular concentration of free calcium ions. Diltiazem is pharmacologically characterized by inotropic and negative chronotropic cardiac effects, which are associated with a vasodilating effect. The existence of the aforementioned inotropic and negative chronotropic cardiac effects have generally prevented the exploitation of the vasodilatory activity of diltiazem.

We have now found, surprisingly, that a class of benzothiazepine esters having structures related to that of diltiazem are endowed with a vasodilating activity while being virtually free of cardiodepressive effects. A selectivity of action follows from this which is particularly interesting with a view to therapeutic use in the treatment of arterial hypertension and disturbances of the cerebral circulation.

Thus according to one aspect of the present invention there are provided compounds of general formula I

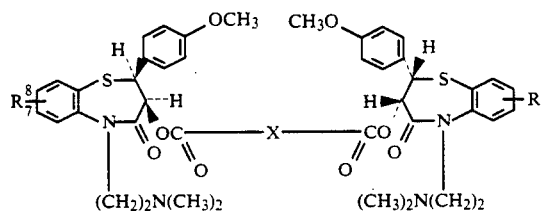

wherein
R represents hydrogen or an electronegative group (preferably a halogen atom, or a nitro, trifluoromethyl or methoxy group); and
X is a hydrocarbyl group containing from 1 to 15 carbon atoms.

Examples of hydrocarbyl groups represented by X include
(i) saturated or unsaturated aliphatic groups (which may be linear or branched chain) containing 1 to 15 carbon atoms,
(ii) wholly aromatic groups containing 1 to 15 carbon atoms, e.g. phenylene groups, and
(iii) groups having both aromatic and aliphatic components, e.g. alkaryl or aralkyl groups containing 1 to 15 carbon atoms.

A specific example of a group of class (iii) is

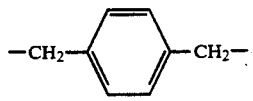

The optional substituents R are preferably in the 7 or 8 positions.

Amongst compounds of formula I which are of particular interest are esters corresponding to malonic, succinic, glutaric, adipic, fumaric, maleic, acetylenedicarboxylic and the phthalic acids (phthalic, iso-phthalic and terephthalic acids).

Compounds of formula I may be prepared by reacting an 1,5-benzothiazepin-4(5H)-one of formula (II)

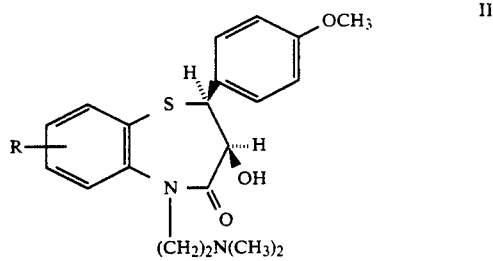

where R is as defined above, with a dicarboxylic acid of formula HOOC.X.COOH (III), where X ia as defined above, or an ester forming derivative thereof e.g. an acyl chloride or imidazolide and the aforementioned preparation provides a further aspect of the invention.

Preferably one mole of (III) is reacted with a molar excess (at least two moles) of II. Most preferably (II) and (III) are reacted in a molar ratio of about 2:1.

The esterification is preferably carried out in a solvent having basic characteristics, for example pyridine. Alternatively, the reaction may be carried out in a solvent having neutral characteristics (for example toluene or dichloromethane), in which case it is preferred for the reaction to be conducted in the presence of an acid acceptor such as triethylamine.

One example of a compound of formula I according to the present invention is the fumaric acid ester Ia (R=H, X=trans—CH═CH—). For the preparation of this substance, the synthesis preferably involves the reaction of two moles of II (R=H) with an excess of fumaryl dichloride in toluene and in the presence of triethylamine. The reaction mixture is kept cold in an inert gas atmosphere for about 1 hour until II has disappeared. At the end of the reaction, the excess acid chloride is hydrolysed in water and ice, and the diester Ia is extracted with a suitable organic solvent.

The compound Ia can be purified by crystallization or converted into a water-soluble salt thereof by addition of a suitable inorganic or organic acid.

The compounds according to the invention can be appropriately formulated in forms suitable for oral or injectable administration, using conventional techniques and excipients such as those reported in Remington's Pharmaceutical Sciences, Mack Pub. Co. York, U.S.A.

Thus according to a further aspect of the invention there are provided pharmaceutical compositions comprising a compound of formula I, as defined above, and a pharmaceutically acceptable excipient.

The invention further provides the use of the compounds of formula I in producing a vasodilating effect in a subject.

The production of compounds according to the invention will now be described in the following examples, which illustrate the invention without representing a limitation thereof.

EXAMPLE 1

Synthesis of
3,3'-[(2E)-(1,4-dioxo-1,4-butenediyl)-bis(oxy)]bis[(+)-cis-5-[2-(dimethylamino)ethyl]-2,3-dihydro-2-(4-methoxyphenyl)-1,5-benzothiazepin-4-(5H)-one] (Ia, R=H; X=trans—CH=CH—)

A solution of 4.0 g of II (R=H) in 60 ml of toluene is cooled to 0° C. with stirring and in a nitrogen atmosphere. 2.4 ml of triethylamine are added, followed by a solution of 0.9 ml of fumaryl dichloride in 15 ml of toluene. The reaction mixture is left for 30 minutes at 0° C., poured into 300 ml of water and ice and extracted with ethyl acetate. By evaporation of the organic phase and trituration in petroleum ether, 3.88 g (88% yield) of product Ia having a melting point of 112°–114° C. and $M^+$ 824 are obtained.

| Elemental analysis for $C_{44}H_{48}N_4O_8S_2$ | | | | |
|---|---|---|---|---|
| | C | H | N | S |
| Calculated % | 64.06 | 5.86 | 6.79 | 7.77 |
| Found % | 63.95 | 5.92 | 6.72 | 7.69 |

EXAMPLE 2

Preparation of Ia hydrochloride

A saturated solution of hydrochloric acid in ethyl ether is added to a solution, cooled to 0° C., of 5.0 g of Ia in 30 ml of acetone, until the pH is acidic. The hydrochloride crystallizes and is recovered by filtration. This gives 5.3 g of product Ia as the hydrochloride having a melting point of 200°–202° C.

| Elemental analysis for $C_{44}H_{48}N_4O_8S_2 \cdot 2HCl$ | | |
|---|---|---|
| | Cl | N |
| Calculated % | 7.90 | 6.24 |
| Found % | 7.75 | 6.20 |

EXAMPLE 3

Synthesis of 3,3'-[(1,4-dioxo-1,4-butanediyl)-bis(oxy)]bis[(+)-cis-5-[2-(dimethylamino)ethyl]-2,3-dihydro-2-(4-methoxyphenyl)-1,5-benzothiazepin-4(5H)-one] (Ib, R=H, X=$(CH_2)_2$).

4.5 ml of succinyldichloride are added with stirring and in a nitrogen atmosphere to a solution of 30 g of II (R=H) in 300 ml of pyridine, cooled to 0° C., and the reaction mixture is warmed to 25° C. After 4 hours, the reaction mixture is poured into 1 l of ice-water in the presence of 1 l of ethyl acetate. The organic phase is washed with water and dried over sodium sulphate. After evaporation of the solvent, the residue is washed with petroleum ether and crystallized from ethyl ether. This gives 30 g (90% yield) of product Ib having a melting point of 112°–115° C. and $M^+$ 826.

| Elemental analysis for $C_{44}H_{50}N_4O_8S_2$ | | | | |
|---|---|---|---|---|
| | C | H | N | S |
| Calculated % | 63.90 | 6.09 | 6.77 | 7.75 |
| Found % | 63.71 | 6.21 | 6.65 | 7.59 |

EXAMPLE 4

Preparation of Ib hydrochloride

A saturated solution of hydrochloric acid in ethyl ether is added at 0° C. to a solution of 6.5 g of Ib in 130 ml of a 1/1 isopropyl ether/acetone mixture, until the pH is acidic. The hydrochloride crystallizes and is recovered by filtration. 6.7 g of product Ib as the hydrochloride having a melting point of 183°–185° C. are obtained.

| Elemental analysis for $C_{44}H_{50}N_4O_8S_2 \cdot 2HCl$ | | |
|---|---|---|
| | Cl | N |
| Calculated % | 7.88 | 6.22 |
| Found % | 7.80 | 6.20 |

EXAMPLE 5

Synthesis of
bis[(+)-cis-5-[2-dimethylamino)-ethyl]-2,3-dihydro-2-(4-methoxyphenyl)-1,5-benzothiazepin-4(5H)-on-3-yl] 1,4-benzenedicarboxylate (Ic, R=H, X=p—$C_6H_4$).

0.8 Ml of triethylamine and 0.55 g of terephthaloyl dichloride are added with stirring and in a nitrogen atmosphere to a solution of 2.0 g of II (R=H) in 30 ml of dichloromethane. After 6 hours, the reaction mixture is poured into 100 ml of ice water and extracted with dichloromethane. The organic phase is washed with $NaHCO_3$ and then with water and finally dried. After evaporation of the solvent, the residue is crystallized from ethyl acetate. This gives 1.89 g (80% yield) of product Ic having a melting point of 213°–215° C. and $M^+$ 874.

| Elemental analysis for $C_{48}H_{50}N_4O_8S_2$ | | | | |
|---|---|---|---|---|
| | C | H | N | S |
| Calculated % | 65.88 | 5.76 | 6.40 | 7.33 |
| Found % | 65.70 | 5.81 | 6.38 | 7.29 |

PHARMACOLOGICAL ACTIVITY

The pharmacological activity of the compounds of the invention is illustrated by the following pharmacological tests:

A. CALCIUM-ANTAGONISTIC ACTIVITY

The calcium-antagonistic activities of the compounds Ia and Ib were evaluated by comparison with that of diltiazem on isolated guinea pig atria and on the isolated portal vein of rats.

1. The atria taken from Hartley-Dunkin guinea pigs of average weight 400–450 g were placed in an isolated organ bath of 15 ml containing a physiological Krebs solution (J. C. Doxey et al., Br. J. Pharmac. 78, 498, 1983) at a temperature of 30°±0.5° and oxygenated by means of a gaseous mixture composed of 95% of $O_2$ and 5% of $CO_2$. The force and frequency of the spontaneous contractions (T. De Gubareff and W. Sleaton Jr., J. Pharm. Exp. Ther., 148, 202, 1965) were recorded by means of an isometric force transducer. The concentration of product required to reduce the contraction force and frequency by 25% ($IC_{25}$) and the relevant $pIC_{25}$ were calculated.

The results reported in Table I demonstrate that the products Ia and Ib are virtually inactive regarding both the force and the frequency of the contractions. In fact, the result reached at the maximum concentration compatible with the solubility limit of the compounds under the adopted experimental conditions ($10^{-5}$ M) is a positive inotropic effect of 6 and 12% respectively and a negative chronotropic effect of 5%.

By contrast, diltiazem shows a significant activity in reducing both the force and the frequency of the contractions at a $pIC_{25}$ value of 6.29 and 6.45 respectively.

2. 2–3 cm strips of portal vein were taken from Sprague-Dawley rats of 220–250 g weight. The organs were placed in an isolated organ bath of 15 ml containing physiological Krebs solution at a temperature of 37°±0.5° C. and oxygenated by means of a gaseous mixture containing 95% of $O_2$ and 5% of $CO_2$ (N. Shoemaker et al., J. Cardiov. Pharm., 9, 173, 1987). After 1 hour of stabilization of the preparation, cumulative doses of compounds Ia and Ib were added and the effect thereof on the force of spontaneous contraction was evaluated.

The concentration of product required to reduce the contraction force by 50% (IC50) and the relevant pIC50 were calculated.

The results reported in Table I demonstrate that the compounds Ia and Ib antagonize the contraction force in a dose-dependent manner. The calculated $pIC_{50}$ values are 5.40 and 5.63 respectively.

Diltiazem inhibits the parameter evaluated at a $pIC_{50}$ value equal to 6.09.

The comparison of the results obtained makes it clear that, although diltiazem is equally active on the two different isolated organs, the compounds Ia and Ib surprisingly display a selective activity on the isolated vessels. In fact, they significantly inhibit the contraction force of the rat portal vein, which shows morphological and functional characteristics of the resistance vessel (J. A. Bven, Circulation Res., 45, 161, 1979; P. Hellstrand, Acta Physiol. Scand. Suppl. 404, 1, 1979), while they turn out to be free of the negative chronotropic and inotropic effects characteristic of diltiazem.

TABLE I

Effect of the compounds Ia and Ib on isolated guinea pig atria and on the isolated rat portal vein

| COMPOUNDS | Isolated guinea pig atria | | Isolated rat portal vein |
|---|---|---|---|
| | Contraction force pIC25 | Frequency pIC25 | Contraction force pIC50 |
| Ia | n.d. | n.d. | 5.40 |
| Ib | n.d. | n.d. | 5.63 |
| Diltiazem | 6.29 | 6.45 | 6.09 | n = 6
n.d. = not determinable

B. HAEMODYNAMICS IN ANAESTHETIZED RATS.

Male Sprague-Dawley rats of average weight 350–400 g, anaesthetized with sodium pentobarbital in an intraperitoneal dose of 60 mg/kg, underwent cannulation for measuring the following parameters: systemic arterial pressure (BP), heart rate (HR) left intraventricular pressure (LVP) and dp/dt.

After recording of the baseline values, the substances were injected by the intravenous route within a time of 30 seconds. The changes in the parameters indicated above were measured at times of 0.5-2-10 and 20 minutes.

The results reported in Table II demonstrate that diltiazem in a dose of 0.7 μmol/kg significantly reduces all the observed parameters. Of particular importance is the effect on the heart rate (−99 bpm) and the contractility of the myocardium (dp/dt −658 mmHg/second), which shows a significant cardiodepressive effect.

Surprisingly, the compound Ia in a dose of 0.7 μmol/kg shows a significant and lasting hypotensive activity without altering the heart rate and contractility parameters, thus showing the absence of the cardiodepressive effect induced by diltiazem. The reduction in LVP, which cannot be correlated with the dp/dt changes, is to be attributed to a diminution of the resistance secondary to a peripheral vasodilatation.

These results, confirm those obtained in vitro and demonstrate for the compound Ia a selective action on the smooth vessel musculature.

TABLE II

Effect of the compound Ia on some haemodynamic parameters in rats under anaesthesia

| Substances | μmol/kg i.v. | Time (minutes) | BP (mmHg) | HR (bpm) | LVP (mmHg) | dp/dt (mmHg/sec) |
|---|---|---|---|---|---|---|
| Ia | 0.35 | 0.5 | −32** | −19 | −29** | −31 |
| | | 2 | −16 | −19 | −11 | −20 |
| | | 10 | +2 | −9 | −2 | −67 |
| | | 20 | −8 | −14 | −11 | −25 |
| | 0.70 | 0.5 | −32** | −19 | −33** | −15 |
| | | 2 | −33** | −11 | −32** | −20 |
| | | 10 | −22** | −13 | −32** | −16 |
| | | 20 | −25** | −9 | −32** | −20 |
| Diltiazem | 0.35 | 0.5 | −21** | −4 | −18* | −150 |
| | | 2 | −1 | +6 | −1 | −25 |
| | | 10 | +6 | +10 | +2 | −17 |
| | | 20 | +1 | +3 | −5 | −183 |
| | 0.70 | 0.5 | −52** | −83** | −46** | −658** |
| | | 2 | −34** | −99** | −24** | −375** |
| | | 10 | −16* | −5 | −4 | −108 |
| | | 20 | +9 | +7 | −7 | −92 | n = 6;
*p < 0.05 (Student's t test)
**p < 0.01 (Student's t test)

C. ACUTE TOXICITY

The acute toxicity of the compounds Ia and Ib was evaluated on rats after administration by the oral and intraperitoneal routes. Sprague-Dawley rats of both sexes (5 male + 5 female) were used for each experimental group. After the treatment, the animals were observed for 14 days and the dose which causes 50% mortality, $LD_{50}$, was calculated by the probit method (D. J. Finney in "Probit Analysis", Cambridge University Press, 3rd Edition, Cambridge, 1971). The results reported in Table III indicate that, after administration by the oral route, the compound Ib shows a $LD_{50}$ comparable with that of diltiazem, while the product Ia turned out to be less toxic. Via the intraperitoneal route, both the compounds turned out to be less toxic than the reference product.

TABLE III

Acute toxicity of compounds Ia and Ib in rats

| COMPOUNDS | $LD_{50}$ (confidence limits p = 0.95) mg/kg | |
|---|---|---|
| | intraperitoneally | orally |
| Ia | 250 (200–339) | >1500 (LDO) |
| Ib | 600 (492–869) | 881 (661–1500) |
| Diltiazem | 137 (49–152) | 720 (611–910) |

FORMULATIONS

The following formulations represent non-limiting examples.

50 mg Vial

Lyophilized vial

Ia, hydrochloride—50 mg

Mannitol—90 mg

Solvent vial

Water for injectable preparations—2.5 ml 150 mg capsules

Ia hydrochloride—150 mg

Lactose—236 mg

Methacrylic acid copolymer—28 mg

Polyethylene glycol 6000—24 mg

Magnesium stearate—12 mg 150 mg tablets

Ia hydrochloride—150 mg

Lactose—420 mg

Methacrylic acid copolymer—35 mg

Polyethylene glycol 6000—30 mg

Magnesium stearate—15 mg

We claim:

1. A compound of formula I

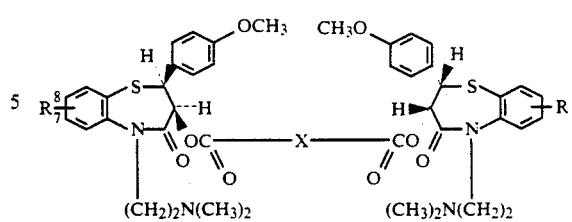

wherein R represents hydrogen, halogen, nitro, trifluoromethyl or methoxy, and X represents —$(CH_2)_n$— wherein n is an integer from 1 to 4, cis- or trans- —(CH=CH)—, —(C≡C)— or o-, m- or p- phenylene.

2. A compound according to claim 1 selected from:
3,3'-[(2E)-(1,4-dioxo-1,4-butenediyl)-bis(oxy)]-bis-[(+)-cis-5-[2-(dimethylamino)ethyl]-2,3-dihydro-2-(4-methoxyphenyl)-1,5-benzothiazepin-4(5H)-one] (Ia, R=H; X=trans —CH=CH—), 3,3'-[(1,4-dioxo-1,4-butanediyl)-bis-(oxy)]-bis[(+)-cis-5-[2-(dimethylamino)ethyl]-2,3-dihydro-2-(4-methoxyphenyl)-1,5-benzothiazepin-4(5H)-one] (Ib, R=H, X=$(CH_2)_2$), and bis[(+)-cis-5-[2-dimethylamino)-ethyl]-2,3-dihydro-2-(4-methoxyphenyl)-1,5-benzothiazepin-4(5H)-on-3-yl] 1,4-benzendicarboxylate (Ic, R=H, X=p-$C_6H_4$).

3. A compound according to claim 1 in the form of a pharmaceutically acceptable salt.

4. A process for producing a compound according to claim 1 which comprises reacting a 1,5-benzothiazepin-4(5H)-one of formula (II)

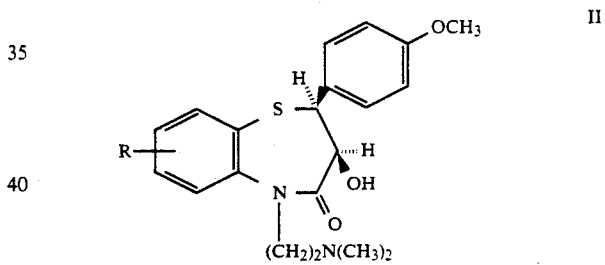

wherein R represents hydrogen, halogen, nitro, trifluoromethyl or methoxy, with a compound selected from the group consisting of dicarboxylic acids of formula HOOC.X.COOH (III), and reactive ester forming derivatives thereof capable of forming an ester group —OCO— by reaction with the —OH of said 1,5-benzothiazepin-4(5H)-one of formula (II), wherein X represents —$(CH_2)_n$— wherein n is an integer from 1 to 4, cis- or trans- —(CH=CH)—, —(C≡C)— or o-, m- or p- phenylene, followed, if desired by conversion into a pharmacologically acceptable salt.

5. A process according to claim 4, wherein said reactive ester forming derivatives are selected from the group consisting of acyl chlorides and imidazolides of dicarboxylic acids of formula HOOC.X.COOH (III).

6. A process according to claim 4 wherein (II) and (III) are reacted in a molar ratio of about 2:1.

7. A pharmaceutical composition for use in obtaining a vasodilatory effect comprising an effective vasodilatory amount of a compound as defined in claim 1 and a pharmaceutically acceptable excipient.

8. A method of producing a vasodilatory effect in a subject which comprises administering an effective amount of a compound as defined in claim 1.

* * * * *